United States Patent [19]
Oda

[11] Patent Number: 5,810,765
[45] Date of Patent: Sep. 22, 1998

[54] IRRIGATION/ASPIRATION APPARATUS

[75] Inventor: Hideo Oda, Gamagori, Japan

[73] Assignee: Nidek Company, Ltd., Japan

[21] Appl. No.: 464,212

[22] Filed: Jun. 5, 1995

[30] Foreign Application Priority Data

Jun. 30, 1994 [JP] Japan .................................. 6-173578

[51] Int. Cl.⁶ .................................................. A61M 1/00
[52] U.S. Cl. ............................... 604/31; 604/22; 604/35; 606/107
[58] Field of Search ............................. 604/30, 31, 27, 604/80, 81, 35, 22; 606/107

[56] References Cited

U.S. PATENT DOCUMENTS

| | | | |
|---|---|---|---|
| 4,180,074 | 12/1979 | Murry et al. | 604/31 X |
| 4,755,168 | 7/1988 | Romanelli et al. | 604/31 X |
| 5,053,002 | 10/1991 | Barlow | 604/30 |
| 5,167,620 | 12/1992 | Ureche et al. | 604/30 X |
| 5,360,398 | 11/1994 | Grieshaber et al. | 604/30 |

FOREIGN PATENT DOCUMENTS 6-38946  5/1994  Japan .

*Primary Examiner*—Mark Bockelman
*Attorney, Agent, or Firm*—Rossi & Associates

[57] ABSTRACT

A irrigation/aspiration apparatus to be used in a cataractal operation comprises an irrigation fluid supply means for supplying an irrigation fluid contained in an irrigation bottle to the patient's eye, and an irrigation fluid aspirating means for aspirating, together with loosened tissues and the like, the irrigation fluid supplied into the patient's eye. The irrigation/aspiration apparatus is characterized by an irrigation flow rate varying means for varying the irrigation rate of the irrigation fluid at which the irrigation fluid supply means supplies the irrigation fluid, and an irrigation flow rate control means for controlling the irrigation flow rate varying means according to the operating condition of the irrigation fluid aspirating means to regulate the irrigation flow rate so that the variation of the pressure in the anterior chamber of the patient's eye is suppressed during the cataractal operation.

4 Claims, 5 Drawing Sheets

| | IRRIGATION MODE | IRRIGATION/ ASPIRATION MODE | IRRIGATION/ASPIRATION PHACOEMULSIFICATION MODE |
|---|---|---|---|
| FIRST POSITION | IRRIGATION | IRRIGATION | IRRIGATION |
| SECOND POSITION | IRRIGATION | IRRIGATION AND ASPIRATION | IRRIGATION AND ASPIRATION |
| THIRD POSITION | IRRIGATION | IRRIGATION AND ASPIRATION | IRRIGATION ASPIRATION AND PHACOEMULSIFICATION |

FIG. 2

IRRIGATION/ASPIRATION APPARATUS

BACKGROUND OF THE INVENTION

1. Field of the Invention

The present invention relates to an irrigation/aspiration apparatus to be used in a cataractal operation for extracting the opaque lens of the eye.

2. Description of the Related Art

Representative methods of cataractal operation are an extracapsular cataract extraction method which extracts the lens nucleus without removing the posterior capsule, and a phacoemulsification method which crushes and emulsifies the lens nucleus with an ultrasonic vibration and aspirates the emulsified lens particles. In carrying out these methods, an irrigation fluid is supplied into the eye and the drainage containing the irrigation fluid, the residual cortex and lens nucleus particles are sucked out by aspiration.

A conventional irrigation/aspiration apparatus for cataractal operation supplies an irrigation fluid at a fixed irrigation flow rate corresponding to an aspiration flow rate.

Generally, the aspiration is aspirated intermittently. Therefore, during operation, the irrigation fluid is supplied and not aspirated in a period, and the irrigation fluid is supplied and aspirated in another period. If the irrigation flow rate is set up suitable according to the aspiration flow rate, there is the possibility that the quantity of the irrigation fluid increases excessively while the irrigation fluid is supplied and not aspirated and the pressure in the anterior chamber rises.

If the irrigation flow rate is lower than the suitable value, the anterior chamber cannot be maintained during aspiration and there is the danger of breaking the posterior capsule and of damaging the corneal endothelium.

SUMMARY OF THE INVENTION

The present invention has been made in view of those problems in the prior art and it is therefore an object of the present invention to provide an irrigation/aspiration apparatus capable of suppressing the variation of the pressure in the anterior chamber of the patient's eye during operation.

With the foregoing object in view, the present invention provides an irrigation/aspiration apparatus comprising:

an irrigation fluid supply means for supplying an irrigation fluid contained in an irrigation bottle to the patient's eye, and an irrigation fluid aspiration means for aspirating, together with loosened tissues and the like. The irrigation/aspiration apparatus is characterized by an irrigation flow rate varying means for varying the irrigation flow rate at which the irrigation fluid supply means supplies the irrigation fluid, and an irrigation flow rate control means for controlling the irrigation flow rate varying means according to the operating condition of the irrigation fluid aspiration means.

In one aspect of the present invention, the irrigation flow rate varying means is an irrigation bottle moving means for moving the irrigation bottle to change the height of the irrigation bottle.

In another aspect of the present invention, the irrigation flow rate varying means comprises an irrigation bottle holding means for holding a plurality of irrigation bottles respectively at different heights in a suspended state, and an irrigation bottle changing means for selectively connecting one of the plurality of irrigation bottles to an irrigation fluid supply passage.

In a further aspect of the present invention, the flow rate varying means comprises an irrigation fluid supply pump for pumping out the irrigation fluid from the irrigation bottle, and a pump driving means for varying the discharge of the irrigation fluid supply pump.

Since the irrigation/aspiration apparatus of the present invention is capable of reducing the difference between the pressure in the anterior chamber of the patient's eye in an irrigation mode and the pressure in the same in an irrigation/aspiration mode, the stability of the depth of the anterior chamber can be improved.

BRIEF DESCRIPTION OF THE DRAWINGS

The above and other objects, features and advantages of the present invention will become more apparent from the following description taken in connection with the accompanying drawings, in which:

FIG. 2 is a table showing foot pedal positions and corresponding modes of operation;

DETAILED DESCRIPTION OF THE PREFERRED EMBODIMENTS

First Embodiment

Figure 1:
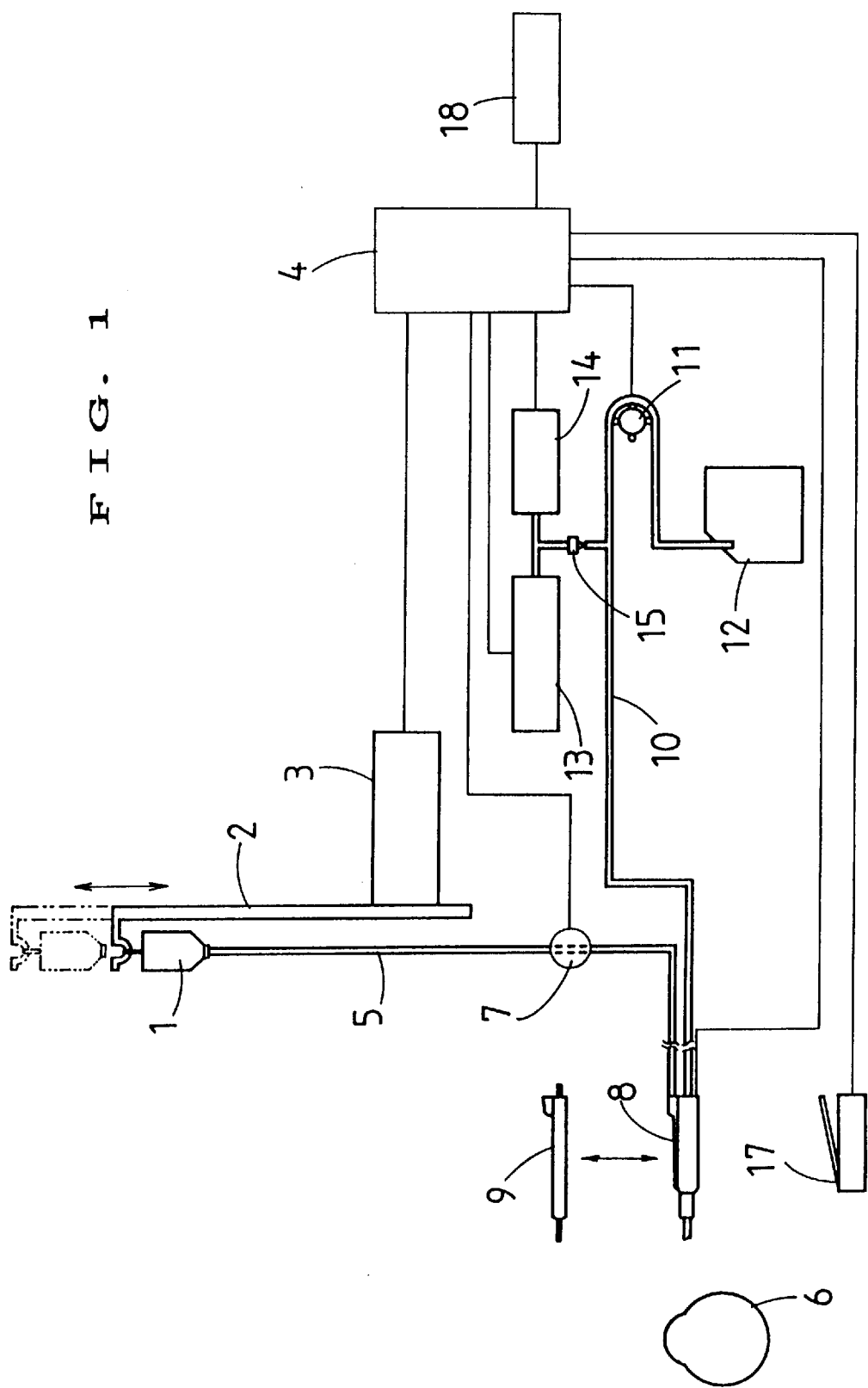
FIG. 1 is a typical view of an irrigation/aspiration apparatus in a first embodiment according to the present invention.

Referring to FIG. 1 showing an irrigation/aspiration apparatus in a first embodiment according to the present invention, an irrigation bottle 1 containing an irrigation fluid, such as balanced salt solution, is suspended from a pole 2 held on the main unit, not shown, of the irrigation/aspiration apparatus so as to be vertically movable. The pole 2 is moved vertically by a pole driving unit 3 comprising a motor and a motor driving circuit. A control unit 4, which controls the operation of the irrigation/aspiration apparatus, gives control signals to the pole driving unit 3 to control the same. When the pole 2 is moved vertically by the pole driving unit 3, the height of the irrigation bottle 1 changes and, consequently, the pressure (=the irrigation flow rate or the irrigation speed) of the irrigation fluid dropping from the irrigation bottle 1 changes accordingly.

The irrigation fluid discharged from the irrigation bottle 1 is supplied to the patient's eye 6 by an irrigation tube 5 having one end connected to the irrigation bottle 1. An irrigation control valve 7 is provided on the irrigation tube 5 and is opened and closed to control the flow of the irrigation fluid.

The other end of the irrigation tube 5 is connected to an ultrasound hand-piece 8 or an irrigation/aspiration hand-piece 9. The ultrasound hand-piece 8 is provided on its extremity with a tip having a suction hole to crush and emulsify the lens nucleus by the agency of ultrasonic vibrations and to aspirate the emulsified lens particles together with the irrigation fluid.

The irrigation/aspiration hand-piece 9 is provided on its extremity with a tip having a suction hole to aspirate the residual cortex and the like together with the irrigation fluid after the lens has been removed. The ultrasound hand-piece 8 or the irrigation/aspiration hand-piece 9 is connected selectively to the irrigation tube 5 according to the stage of operation or the method of operation.

The drainage containing the crushed lens particles and sucked by the ultrasound hand-piece 8 or the irrigation/aspiration hand-piece 9 is drained through an aspiration tube 10. A suction pump 11 for generating a suction is disposed at the rear part of the aspiration tube 10. The control unit 4 controls the operation of the suction pump 11 to regulate the aspiration flow rate. The irrigation thus sucked is drained into a drainage bag 12.

A vacuum sensor 13 and a vent valve 14 are connected by a fitting 15 to the aspiration tube 10. The vacuum sensor 13 detects the vacuum level continuously and, upon the increase of the vacuum level beyond a set value, the control unit 4 provides a control signal to open the vent valve 14, whereby air is introduced into the aspiration tube 10 to lower the vacuum.

A foot pedal 17 is operated to select an irrigation mode or an irrigation/aspiration mode, and to start and stop the phacoemusifying operation of the ultrasound hand-piece 8. The irrigation mode, the irrigation/aspiration mode or the emulsification mode can be selected by depressing the foot treadle of the foot pedal 17 to a corresponding position (FIG. 2). An input unit 18 is provided with switches for specifying various operating modes including the irrigation mode, the irrigation/aspiration mode and the phacoemulsification mode, and for specifying operating conditions.

In operation, after preparing the irrigation/aspiration apparatus for a cataractal operation, the switches of the input unit 18 are operated to specify an irrigation flow rate of the irrigation fluid, an aspiration flow rate, a vacuum level and the like. The irrigation flow rate of the irrigation fluid is determined by adjusting the height of the irrigation bottle 1 from the patient's eye 6 by operating a pole moving switch of the input unit 18 to move the pole 2 vertically by the pole moving unit 3. After the preparation of the irrigation/aspiration apparatus for a cataractal operation has been completed, the cataractal operation is started.

The operation of the irrigation/aspiration apparatus will be described on an assumption that the irrigation/aspiration apparatus is applied to a cataractal operation of a method comprising sequential steps of incising the sclera, incising the anterior capsule and emulsifying and aspirating the lens particles with the ultrasound hand-piece 8. In this case, the irrigation/aspiration apparatus is set in an irrigation/aspiration/phacoemulsification mode.

The operator incises the sclera and the anterior capsule observing the patient's eye 6 with an operative microscope, and then the operator inserts the tip of the ultrasound hand-piece 8 through the incision into the patient's eye 6. When inserting the tip into the patient's eye 6, the irrigation control valve 7 is opened by depressing the foot treadle of the foot pedal 17 to a position 1 to supply the irrigation fluid. The tip of the ultrasound hand-piece 8 is inserted into the patient's eye 6, the patient's eye 6 is irrigated with the irrigation fluid, and the height of the irrigation bottle 1 is adjusted so that an appropriate depth is secured for the anterior chamber.

After an appropriate depth is secured for the anterior chamber, the lens nucleus is crushed and emulsified, and then the emulsified lens particles is aspirated. When the foot treadle of the foot pedal 17 is depressed to a second position or a third position to give a signal to the control unit 4, the control unit 4 actuates the suction pump 11 to aspirate the drainage through the suction hole of the tip of the ultrasound hand-piece 8 and the aspiration tube 10 by a suction produced by the suction pump 11. When the foot treadle of the foot pedal 17 is depressed to the position 3, the control unit 4, in addition to actuating the suction pump 11, makes the ultrasound hand-piece 8 generate ultrasonic vibrations to crush and emulsify the lens nucleus.

Upon the reception of the signal from the foot pedal 17, the control unit 4 actuates the suction pump 11 and, at the same time, activates the pole moving unit 3 so as to raise the irrigation bottle 1 by a distance necessary for increasing the pressure of the irrigation fluid to increase the irrigation flow rate of the irrigation fluid by a value necessary for compensating the aspiration flow rate. Then, the anterior chamber is irrigated with the irrigation fluid at an increased irrigation flow rate to compensate the aspiration flow rate. The increase in the irrigation flow rate corresponding to the aspiration flow rate suffices to maintain a desired condition for the operation. Since there is a predetermined correlation between the irrigation pressure (irrigation flow rate) and the height of the irrigation bottle 1, the control unit 4 controls the pole moving unit 3 on the basis of the predetermined correlation. The displacement of the pole 2 corresponding to a change in the aspiration flow rate may be determined by using a simple table.

When the foot treadle of the foot pedal 17 is moved to the position 1 or the free position, the control unit 4 stops the suction pump 11 to stop aspiration, and sends a signal to the pole moving unit 3 to move the pole 2 downward so that the irrigation bottle 1 is lowered by a distance equal to the distance for which the irrigation bottle 1 was raised to compensate the aspiration flow rate.

Irrigation and aspiration are performed intermittently during the operation according to the condition of the patient's eye 6 and the condition of aspiration. The irrigation/aspiration apparatus increases the irrigation flow rate according to the aspiration flow rate when the drainage is aspirated, and reduces the irrigation flow rate when aspiration is stopped. Therefore, the variation of the pressure in the anterior chamber of the patient's eye 6 can be suppressed and hence the anterior chamber can be secured in an appropriate condition.

After the emulsified lens particles has been completely aspirated out of the capsule by using the ultrasound hand-piece 8, the ultrasound hand-piece 8 is disconnected from the irrigation tube 5 and the irrigation/aspiration hand-piece 9 is connected to the irrigation tube 5 to remove the residual cortex by intermittent irrigation and aspiration, in which the irrigation bottle 1 is raised when aspiration is started and lowers the irrigation bottle 1 when aspiration is stopped to stabilize the pressure of the irrigation fluid in the anterior chamber of the patient's eye 6.

Second Embodiment

In the first embodiment, the pole 7 suspending the irrigation bottle 1 is moved vertically to adjust the irrigation flow rate. In the second embodiment, a plurality of irrigation bottles are used for adjusting the pressure of the irrigation fluid.

Figure 3:
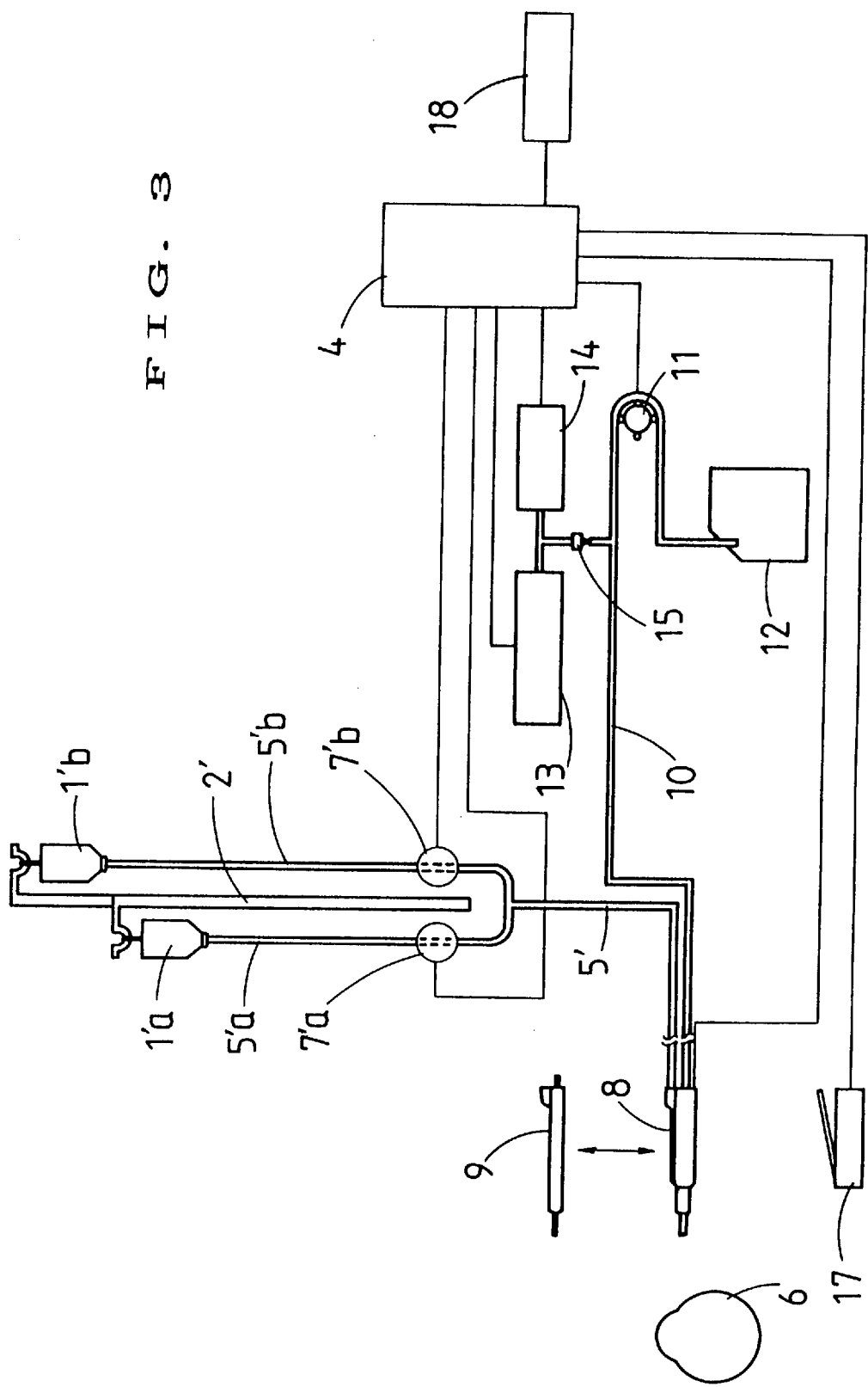
FIG. 3 is a typical view of an irrigation/aspiration apparatus in a second embodiment according to the present invention.

In FIG. 3 showing an irrigation/aspiration apparatus in a second embodiment according to the present invention, parts like or corresponding to those of the first embodiment are designated by the same reference numerals and the description thereof will be omitted to avoid duplication.

Referring to FIG. 3, two irrigation bottles 1'$a$ and 1'$b$ are suspended respectively at different heights from a pole 2'. The difference between the respective heights of the irrigation bottles 1'$a$ and 1'$b$ corresponds to an increase in the irrigation flow rate necessary for compensating an aspiration flow rate.

An irrigation tube 5'a has one end connected to the irrigation bottle 1'a and the other end connected to one end of an irrigation tube 5'. The other end of the irrigation tube 5' is connected to an ultrasound hand-piece 8 or an irrigation/aspiration hand-piece 9. An irrigation tube 5'b has one end connected to the irrigation bottle 1'b and the other end connected to one end of the irrigation tube 5'. A first irrigation control valve 7'a and a second irrigation control valve 7'b are provided on the irrigation tubes 5'a and 5'b, respectively. The irrigation control valves 7'a and 7'b are opened or closed according to a control signal provided by a control unit 4.

In operation, when the foot treadle of a foot pedal 17 is depressed to a position 1, the control unit 4 provides control signals to close the second irrigation control valve 7'b and to open the first irrigation control valve 7'a to supply the irrigation fluid from the irrigation bottle 1'a at the lower position to the patient's eye 6.

When the foot treadle of the foot pedal 17 is depressed to a second position or a third position, the control unit 4 provides control signals to actuate a suction pump 11 to produce a suction and to open the second irrigation control valve 7'b to supply the irrigation fluid from the irrigation bottle 1'b at the higher position. When aspiration is stopped, the control unit 4 provides control signals to close the second irrigation control valve 7'b and to open the first irrigation control valve 7'a to supply the irrigation fluid from the irrigation bottle 1'a at the lower position.

Thus, the second embodiment connects the irrigation bottle 1'b at the higher position to the irrigation tube 5' when aspiration is started and connects the irrigation bottle 1'a at the lower position to the irrigation tube 5' when aspiration is stopped to change the irrigation flow rate so that the variation of the pressure in the anterior chamber of the patient's eye 6 is suppressed.

Third Embodiment

In the first and the second embodiment, the irrigation fluid is supplied from the irrigation bottle or the irrigation bottles suspended from the pole by gravity. In the third embodiment, the irrigation fluid is supplied by a pump and the operation of the pump is controlled to change the irrigation flow rate.

Figure 4:
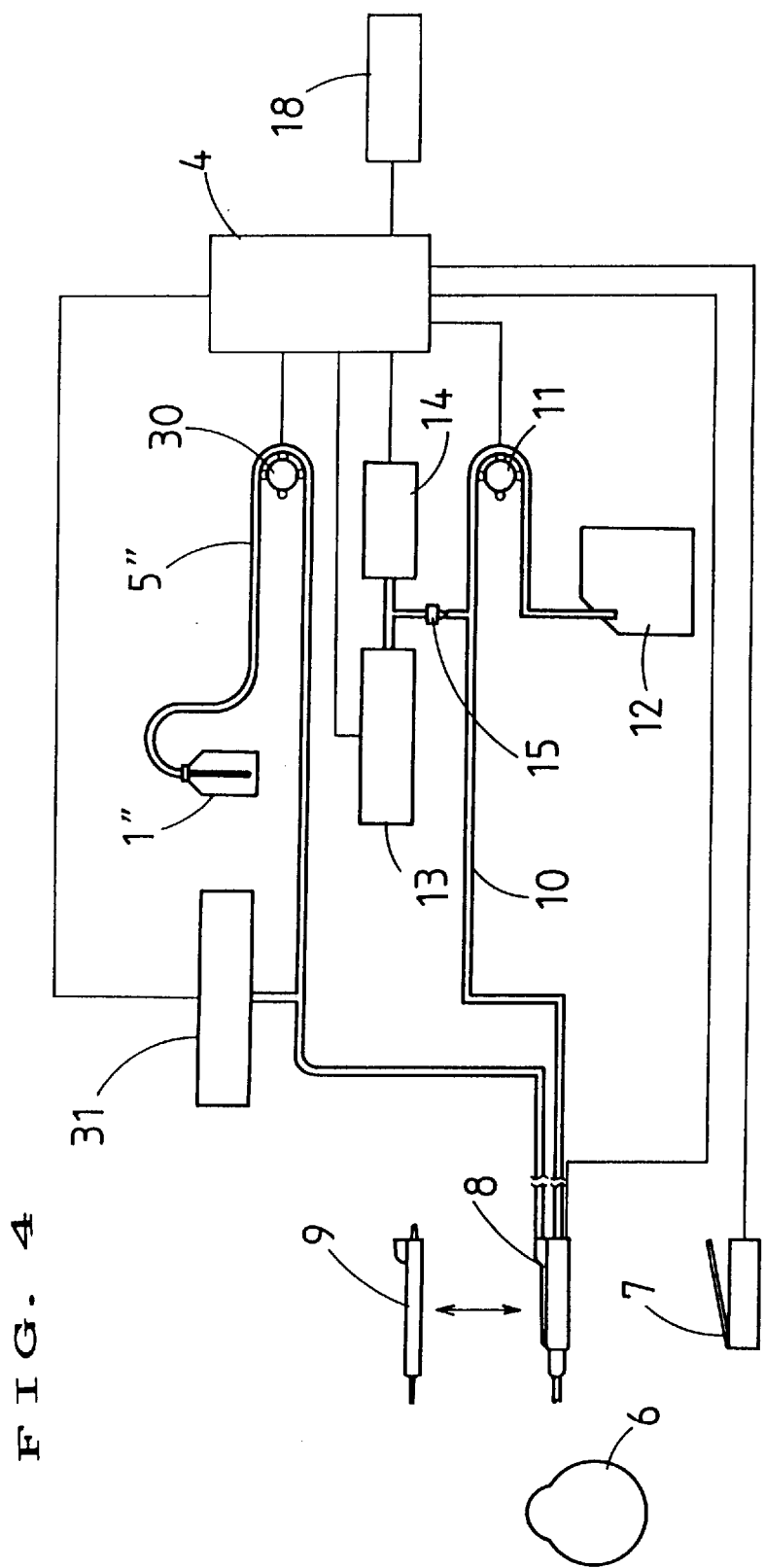
FIG. 4 is a typical view of an irrigation/aspiration apparatus in a third embodiment according to the present invention.

In FIG. 4 showing an irrigation/aspiration apparatus in the third embodiment according to the present invention, parts like or corresponding to those of the first embodiment are designated by the same reference numerals and the description thereof will be omitted to avoid duplication.

Referring to FIG. 4, one end of an irrigation tube 5" is inserted in an irrigation bottle 1" containing an irrigation fluid. An irrigation pump 30 is provided on the irrigation tube 5" to supply the irrigation fluid from the irrigation bottle 1" through an ultrasound hand-piece 8 or an irrigation/aspiration hand-piece 9, connected to the other end of the irrigation tube 5" into the patient's eye 6.

A pressure sensor 31 connected to the irrigation tube 5" detects the pressure of the irrigation fluid in the irrigation tube 5".

When the foot treadle of a foot pedal 17 is depressed to a first position for irrigation, a control unit 4 actuates an irrigation pump 30 to supply the irrigation fluid to the patient's eye 6 at a predetermined irrigation flow rate. While the irrigation fluid is being supplied, the pressure sensor 31 detects the pressure of the irrigation fluid in the irrigation tube 5" and gives a detection signal to the control unit 4. The control unit 4 controls the discharge of the irrigation pump 30 on the basis of the detection signal given thereto from the pressure sensor 31 so that the pressure of the irrigation fluid in the irrigation tube 5" is adjusted to a predetermined value.

When the foot treadle of the foot pedal 17 is depressed to a second position or a third position, a suction pump 11 is actuated for aspiration. Then, the control unit 4 controls the irrigation pump 30 so that the irrigation flow rate of the irrigation fluid are increased according to the irrigation flow rate.

When the foot treadle of the foot pedal 17 is returned to the first position, the control unit 4 stops the suction pump 11 to stop aspiration and controls the discharge of the irrigation pump 30 so that the irrigation flow rate of the irrigation fluid is adjusted to the predetermined values only for irrigation.

Thus, the discharge of the irrigation pump 30 is controlled to vary the irrigation flow rate of the irrigation fluid according to the operating mode to suppress the variation of the pressure in the anterior chamber of the patient's eye 6.

Figure 5:
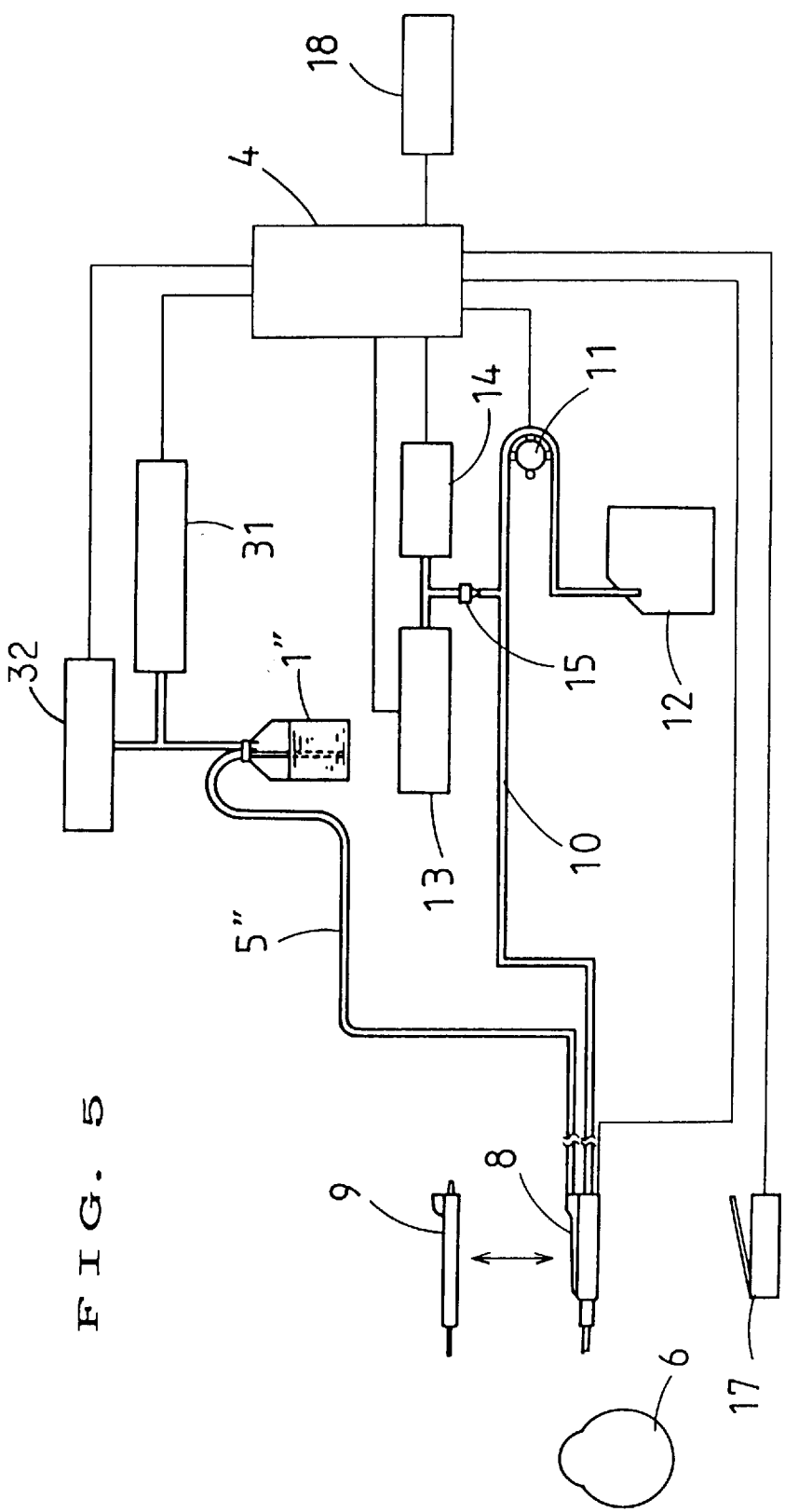
FIG. 5 is a typical view of a modification of the irrigation/aspiration apparatus in the third embodiment.

In a modification of the irrigation/aspiration apparatus in the third embodiment, illustrated in FIG. 5 an air pump capable of supplying compressed air, such as a compressor, may be connected to the irrigation bottle 1' instead of the irrigation pump 30, and the pressure of the compressed air may be controlled to regulate the irrigation flow rate of the irrigation fluid.

The present invention is not limited in its application to the preferred embodiments specifically described herein. For example, an irrigation cannula may be used instead of the ultrasound hand-piece or the irrigation/aspiration hand-piece to irrigate the patient's eye with the irrigation fluid.

Although the invention has been described in its preferred forms with a certain degree of particularity, obviously many changes and variations are possible therein. It is therefore to be understood that the present invention may be practiced otherwise than as specifically described herein without departing from the scope and spirit thereof.

What is claimed is:

1. An irrigation/aspiration apparatus for ophthalmic surgery comprising:

an irrigation means, including an irrigation hand-piece, for supplying an irrigation fluid contained in an irrigation bottle to a patient's eye;

an irrigation flow rate varying means for varying the irrigation flow rate of the irrigation fluid to the irrigation hand-piece in response to a flow rate control signal;

an aspiration means, including an aspiration pump, for aspirating the irrigation fluid with removed tissues from the patient's eye in response to an aspiration control signal;

a control means for respectively supplying the flow rate control signal and the aspiration control signal to the irrigation flow rate varying means and the aspiration means; and input means for supplying an operation control signal to the control means;

wherein the control means controls the operation of the irrigation flow rate control means and the aspiration means, in response to the operation control signal, to maintain the biocavity pressure and capacity of the anterior chamber of the patients's eye at substantially constant levels when the irrigation means is operated alone or simultaneously with the aspiration means.

2. The irrigation/aspiration apparatus according to claim 1, wherein the irrigation flow rate varying means comprises an irrigation bottle moving means for automatically varying the height of the irrigation bottle with respect to the patient's eye in response to the irrigation flow rate control signal.

3. The irrigation/aspiration apparatus according to claim 1, wherein the irrigation flow rate varying means comprises an irrigation bottle holding means for holding a plurality of irrigation bottles at different heights with respect to the patient's eye in a suspended state, and an irrigation bottle changing means for selectively connecting one of the plurality of irrigation bottles to an irrigation fluid supply passage of the irrigation means in response to the irrigation flow rate control signal.

4. The irrigation/aspiration apparatus according to claim 1, wherein the irrigation flow rate varying means comprises an irrigation fluid supply pump for pumping out the irrigation fluid from the irrigation bottle, and a pump driving means for varying the discharge rate of the irrigation fluid supply pump in response to the irrigation flow rate control signal.

* * * * *